United States Patent
Luce

(10) Patent No.: US 6,817,981 B2
(45) Date of Patent: Nov. 16, 2004

(54) METHOD FOR ELIMINATING ERROR IN TONOMETRIC MEASUREMENTS

(75) Inventor: David A. Luce, Clarence Center, NY (US)

(73) Assignee: Reichert, Inc., Depew, NY (US)

( * ) Notice: Subject to any disclaimer, the term of this patent is extended or adjusted under 35 U.S.C. 154(b) by 117 days.

(21) Appl. No.: 10/186,540

(22) Filed: Jul. 1, 2002

(65) Prior Publication Data

US 2004/0002640 A1 Jan. 1, 2004

(51) Int. Cl.[7] ............................................. A61B 3/16
(52) U.S. Cl. ..................................................... 600/399
(58) Field of Search ................................. 600/399, 401, 600/405, 476; 351/205, 221

(56) References Cited

U.S. PATENT DOCUMENTS

| | | | |
|---|---|---|---|
| 4,621,644 A | * 11/1986 | Eilers | 600/405 |
| 4,624,235 A | * 11/1986 | Krabacher et al. | 600/405 |
| 5,070,875 A | * 12/1991 | Falck et al. | 600/405 |
| 5,474,066 A | 12/1995 | Grolman | |
| 6,159,148 A | 12/2000 | Luce | |
| 6,419,631 B1 | 7/2002 | Luce | |
| 6,537,215 B2 | * 3/2003 | Miwa | 600/405 |
| 2002/0103427 A1 | * 8/2002 | Miwa et al. | 600/401 |

* cited by examiner

Primary Examiner—Mary Beth Jones
Assistant Examiner—Brian Szmal
(74) Attorney, Agent, or Firm—Hodgson Russ LLP

(57) ABSTRACT

A novel tonometry method wherein measured intraocular pressure corresponding to inward applanation of the cornea and corneal hysteresis derived from a pressure differential associated with inward and outward applanation events in the same measurement pulse allows comparison with a predetermined population normality function to avoid corneal effects so that the actual status of intraocular pressure can be ascertained. A dual mode non-contact tonometer allows selection between a standard measurement mode for patient comfort and an alternate measurement mode wherein pressure-time characteristics of the fluid pulse are varied to allow additional observation of corneal hysteresis associated with the dynamic measurement process for carrying out the novel tonometry method. Corresponding tonometry method embodiments include a method adapted for a contact tonometer and a method based on a pair of non-contact tonometer measurements taken using different air pulse pressure ramp rates.

18 Claims, 7 Drawing Sheets

METHOD FOR ELIMINATING ERROR IN TONOMETRIC MEASUREMENTS

FIELD OF THE INVENTION

The present invention relates generally to the field of ophthamic instruments, and particularly to a novel tonometric measurement method applicable by both contact and non-contact tonometers.

BACKGROUND OF THE INVENTION

Tonometers for measuring IOP (intraocular pressure) were originally developed as "contact" type instruments, meaning that a portion of the instrument is brought into contact with the cornea during the measurement procedure. A well-known instrument of this type is the Goldmann applanation tonometer originally developed during the 1950s. The GAT measures the force required to flatten ("applanate") a known area of the cornea, and is used today as a standard against which other types of tonometers are calibrated and compared to assess measurement accuracy.

Patient discomfort and the requirement to use anesthesia related to contact tonometers such as the GAT led to the development of "non-contact" tonometers (NCTs) which operate by directing an air pulse at the cornea to cause applanation. Typically, the air pulse is generated by a solenoid driven pump mechanism and directed through a narrow fluid discharge tube at the cornea. As the cornea is deformed by the fluid pulse, an opto-electronic system monitors the cornea by detecting corneally reflected light from a beam incident upon the cornea, and a peak detector signal occurs at the moment of applanation when the reflecting surface of the cornea is flat.

In state of the art NCTs, a pressure transducer detects a plenum pressure in the pump mechanism as the pulse is generated and provides a plenum pressure signal proportional to the plenum pressure. The plenum pressure signal and applanation signal are processed to determine the plenum pressure at the moment of applanation. The plenum pressure at applanation is converted to an IOP value in units of mmHg (millimeters mercury) using a regression equation developed and stored in instrument memory during clinical calibration relative to GAT as a reference. A primary index of an NCT's reliability is the standard deviation of differences $S_d$ of matched pairs of NCT and GAT clinical readings.

While NCTs provide reasonably reliable IOP measurements, IOP readings are occasionally falsely inflated because some of the air pulse energy is expended "bending" the corneal tissue itself, as opposed to displacing intraocular fluid pressing on the cornea. Intuitively, a cornea that is very rigid is more likely to cause a falsely elevated pressure reading because more air pulse energy is required to achieve applanation. In fact, several recent studies indicate that physical properties of the cornea can have a significant impact on NCT readings. See, for example, Copt R-P, Tomas R, Mermoud A, *Corneal Thickness in Ocular Hypertension, Primary Open-Angle Glaucoma, and Normal Tension Glaucoma*, Arch Ophthalmol. Vol. 117:14–16 (1999); Emara B, Probst L E, Tingey D P, Kennedy D W, et al., *Correlation of Intraocular Pressure and Central Corneal Thickness in Normal Myopic Eyes After Laser in situ Keratomileusis*; J Cataract Refract Surg, Vol. 24:1320–25 (1998); Stodtmeister R. *Applanation Tonometry and Correction According to Corneal Thickness*, Acta Ophthalmol Scand, Vol. 76:319–24 (1998); and Argus W A, *Ocular Hypertension and Central Corneal Thickness*, Ophthalmol, Vol. 102:1810–12 (1995). For persons with relatively thick corneas, IOP values measured under prior art methodology can differ significantly from "true" IOP. Heretofore, attempts to correct measured IOP for corneal thickness effects have typically involved measuring corneal thickness by additional instrument means and correcting measured IOP by an amount based upon the measured corneal thickness. U.S. Pat. No. 5,474,066 issued Dec. 12, 1995 to Grolman ascribes to this approach.

A weakness with respect to corrections based on corneal thickness is that corneal thickness is a static parameter that may or may not be a reliable indicator of a cornea's rigidity in response to dynamic loading by an air pulse or other means of applying force to cause applanation. Stated differently, corneas having the same thickness may exhibit different rigidity responses under static or dynamic loading due to differences in the corneal tissue itself. The present applicant, in his U.S. patent application Ser. No. 09/553,111, now U.S. Pat. No. 6,419,631, describes a non-contact tonometry method wherein two plenum pressures are taken into account for correlation to IOP, the first corresponding to an applanation state of the cornea upon inward deformation by an air pulse and the second corresponding to an applanation state of the cornea as it returns from a brief concave state to its normal convex state. In accordance with the described method, it is assumed that corneal rigidity force components associated with inward and outward deformation essentially cancel each other out, and the IOP measurement value is taken either by correlating the inward and outward plenum pressures to IOP based on two separate regression equations and averaging the resultant pair of IOP values, or by averaging the inward and outward plenum pressures and correlating the average pressure to IOP using a single regression equation. While this method is an improvement over the prior art, it is based on an observance of the second applanation event, which is an accidental by-product of excess impulse energy being delivered to the eye beyond the threshold level necessary to achieve the first applanation event. This excess energy is largely considered undesirable by those skilled in the art because it causes patient discomfort during testing. Consequently, developers of non-contact tonometers have sought to minimize excess impulse energy, for example by shutting off or reversing the pump driver at or before the first applanation event, building a pressure release valve or the like into the pump system, and by altering the shape of the pressure ramp itself. In this regard, please see U.S. Pat. Nos. 5,779,633; 5,165,408; and 6,159,148.

Thus, the in/out tonometry method described above suffers in certain respects. The method itself relies on dissipation of the fluid pulse in an uncontrolled manner, such that the plenum pressure as a function of time forms an asymmetrical curve about a peak pressure associated with the pump compression stroke. This fact to some extent undermines the basic assumption of force cancellation in the dynamic system. Also, the use of a non-contact tonometry method that requires delivery of excess impulse energy to the eye is largely incompatible with non-contact tonometers designed to reduce air puff discomfort felt by the patient, and may be unnecessary in situations where the patient's IOP is well within a normal range. Moreover, the in/out tonometry method described above is specific to non-contact tonometers, and does not address the problem of corneal rigidity effects as they relate to contact methods of tonometry.

SUMMARY OF THE INVENTION

Therefore, it is an object of the present invention to provide a tonometry method that essentially eliminates measurement error associated with corneal rigidity to provide a measurement that gives the ophthalmic practitioner improved information regarding whether the patient's true IOP is abnormally high or low.

It is another object of the present invention to provide a tonometry method in accordance with the object stated above that is applicable by both contact and non-contact tonometers.

The invention is preferably embodied in a non-contact tonometer of a general type comprising a fluid pump system, a fluid discharge tube in communication with the fluid pump system for directing a fluid pulse at a patient's eye to cause applanation of the cornea, applanation detection means for monitoring the cornea to detect applanation caused by the fluid pulse, means for determining a fluid pressure within a plenum chamber of the fluid pump system at a moment when the cornea reaches applanation, and processing means for correlating the plenum pressure with an intraocular pressure of the patient's eye. The non-contact tonometer is provided with two measurement modes characterized by different current versus time behavior for the drive current supplied to a proportional solenoid of the fluid pump system, resulting in different plenum pressure versus time behavior and different action by the fluid pulse in the two modes.

In a standard measurement mode, the solenoid drive current increases linearly with time until corneal applanation is detected, at which time the drive current is shut off. This provides a non-linear pressure ramp up to applanation for patient comfort. The plenum pressure at applanation is correlated to IOP in a well-known manner.

In an alternate measurement mode that is novel, the solenoid drive current increases linearly with time until the cornea has been deformed through a first state of applanation to a state of concavity, and then the drive current decreases linearly with time at the same rate as it increased. While the alternate measurement mode is less comfortable for the patient than the standard measurement mode, it allows for observation of plenum pressure at a first or inward applanation event (as in the standard mode) and at a second or outward applanation event occurring as the cornea returns from its concave state back toward its normal convex state. In accordance with a tonometry method of the present invention, a measurement data point comprising an IOP value based on the plenum pressure at inward applanation and a hysteresis value calculated as a difference in IOP values based on the respective plenum pressures at inward and outward applanation. The alternate measurement mode provides a two-dimensional tonometric measurement wherein the first dimension depends on the force necessary to applanate the cornea and the second dimension depends on physical properties of the cornea. For evaluation purposes, the two-dimensional measurement data point is compared with a normal functional relationship between the measured IOP and hysteresis quantities to determine the degree of difference of measured IOP from normality. For example, an "excess ocular pressure" (EOP) can be reported. The normal functional relationship is predetermined during instrument calibration by fitting to clinical trial data taken with respect to a statistically large population of eyes, and is stored in instrument memory.

The general two-dimensional approach to tonometric measurement used in the alternate measurement mode is applicable to both non-contact and contact tonometers. A contact tonometer embodying the present invention includes a contact tip driven inward on the cornea by a linear proportional solenoid at constant velocity through a predetermined displacement to a maximum displacement and then outward at a reverse constant velocity of the same magnitude. The force (proportional to the solenoid drive current) associated with the predetermined displacement position during the inward movement and the force associated with the predetermined displacement position during the outward movement are different, their difference representing the degree of corneal hysteresis.

Another tonometry method embodiment involves taking a pair of measurements on an eye using a non-contact tonometer having a fast pressure ramp mode and a slow pressure ramp mode to detect the rate-dependent hysteresis. The measurements are preferably synchronized relative to a cardiac pulse cycle of the patient because the cardiac pulse cycle is known to cause fluctuations in measured IOP.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
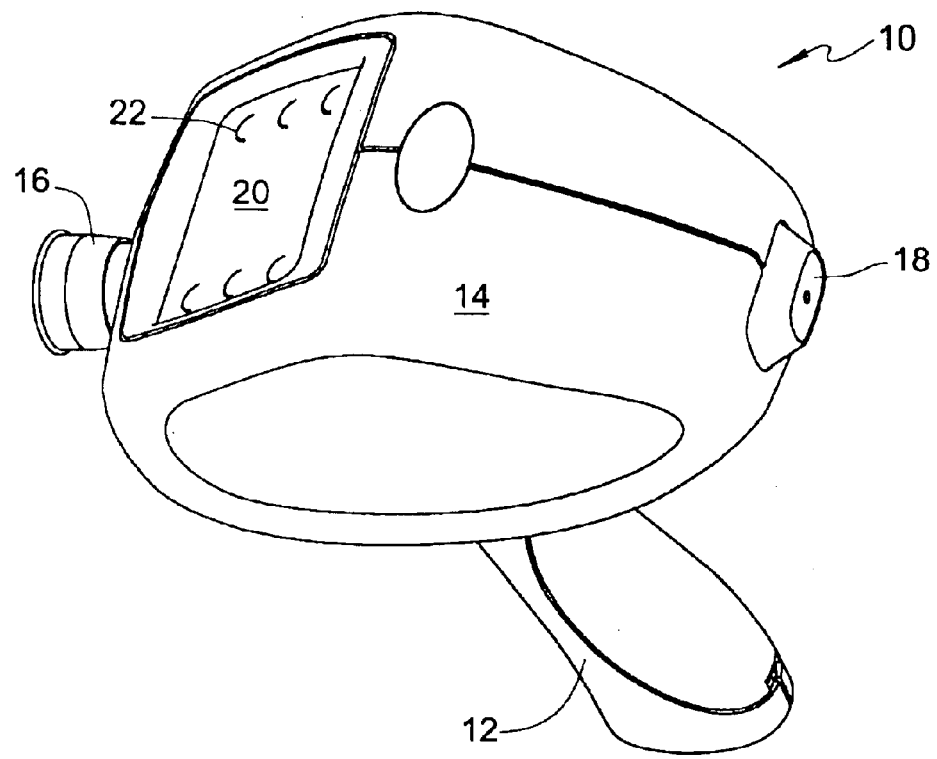
FIG. 1 is a perspective view of a non-contact tonometer embodying the present invention.

FIG. 1 of the drawings shows a handheld non-contact tonometer (NCT) 10 embodying the present invention. While the method of the present invention is described in the context of a handheld NCT, it can also be embodied in a table-top NCT. Moreover, the method of the present invention is applicable to either an NCT or a contact-type tonometer. NCT 10 includes a handle portion 12 and a head portion 14 at the top of the handle portion. Handle portion 12 houses a rechargeable power source for energizing alignment and tonometric measurement systems carried by head portion 14. Also visible in FIG. 1 is an operator eyepiece 16 at one end of head portion 14, a front window 18 at an opposite end of head portion 14 for facing a patient, and a liquid crystal display 20 with pushbutton control overlay 22 angled toward the operator near operator eyepiece 16.

Figure 2:
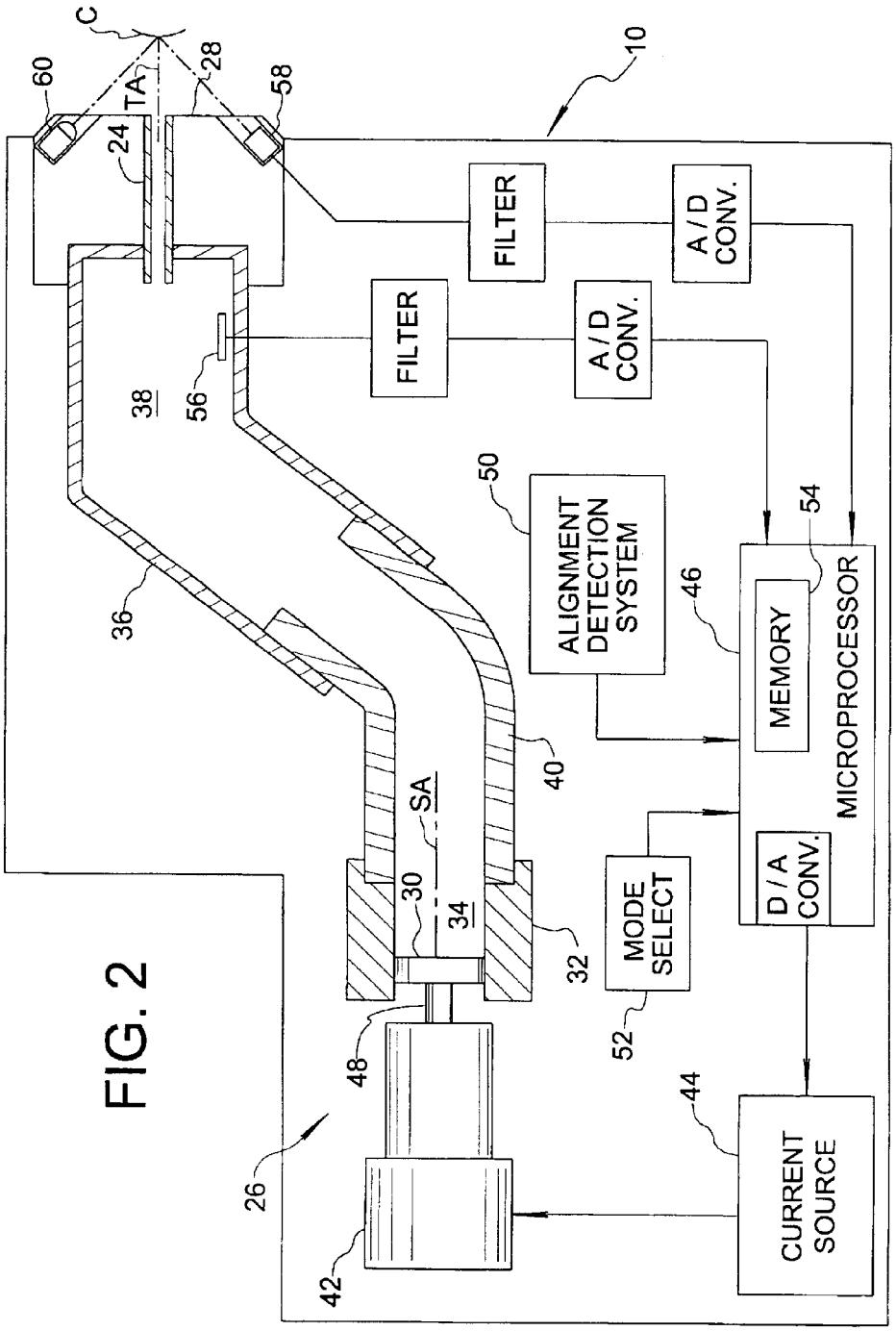
FIG. 2 is a schematic block diagram of the non-contact tonometer shown in FIG. 1.

FIG. 2 provides a schematic representation of the alignment and tonometric measurement systems housed by head portion 14. NCT 10 is operable to discharge a fluid pulse through a fluid discharge tube 24 aligned along a test axis TA to cause observable deformation of a patient's cornea C for purposes of measuring intraocular pressure. The fluid pulse is generated by a fluid pump system 26 communicating with fluid discharge tube 24, which extends through a nosepiece 28. Fluid pump system 26 preferably comprises a piston 30 axially movable relative to a cylinder 32 along a stroke axis SA for compressing fluid within an internal compression chamber 34 defined thereby, a housing 36 defining an internal plenum chamber 38, and a flow tube 40 providing a fluid conduit from compression chamber 34 to plenum chamber 38. Fluid discharge tube 24 is mounted through the wall of housing 36 for guiding pressurized fluid from plenum chamber 38 along test axis TA directed at patient cornea C.

A linear proportional solenoid 42 is operatively connected to piston 30 for causing axially directed movement of piston 30 relative to cylinder 32. A linear proportional solenoid is preferred because it is a specialized type of linear motor wherein the output driving force is proportional to the energizing current, and is most often used in connection with control valves. However, the drive means employed by fluid pump system 26 is not intended to be limited to this particular drive means, as other drive means such as rotary solenoids may possibly be used. Proportional solenoid 42 is connected to a current source 44 which supplies energizing current to the proportional solenoid under the control of a microprocessor 46. A suitable linear proportional solenoid is a LEDEX® Linear Shift Solenoid Part No. 197887-001. As can be seen in FIG. 2, piston 30 is fixed for travel with a plunger 48 of proportional solenoid 42, as by threaded attachment or by fitted attachment with or without mechanical fasteners or adhesives.

Linear proportional solenoid 42 remains de-energized and piston 30 remains at rest until proper positioning of discharge tube 24 relative to cornea C is achieved as determined by an alignment detection system 50 connected to microprocessor 46. Alignment detection system 50 can be any suitable system, for example an alignment system as taught in commonly owned U.S. Pat. Nos. 4,881,807 and 6,361,495. Once alignment is achieved, microprocessor 46 provides a signal used by current source 44 to provide the driving current according to one of a plurality of preprogrammed ramp forms, as will now be described below.

Figure 3:
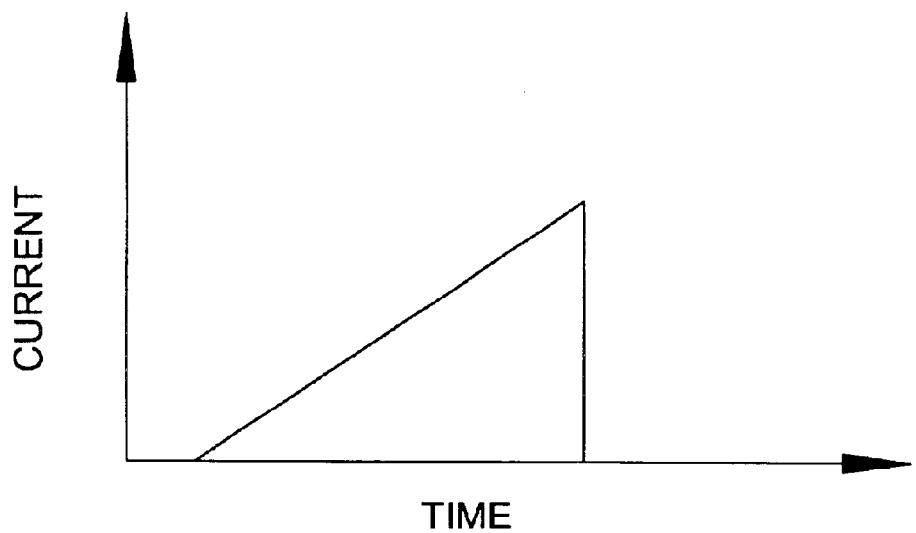
FIG. 3 is a graph of solenoid energizing current versus time in a standard operational mode of the non-contact tonometer.
Figure 5:
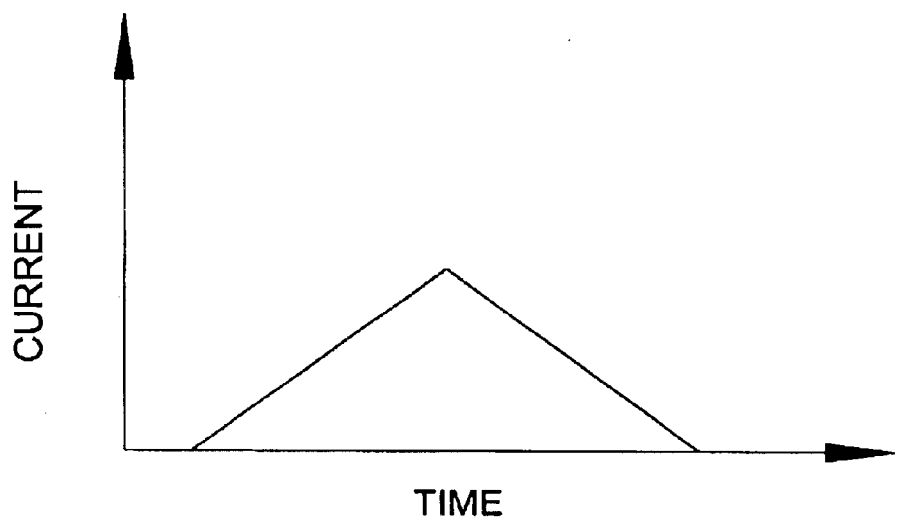
FIG. 5 is a graph of solenoid energizing current versus time in an alternate operational mode of the non-contact tonometer.

A measurement mode control function is part of a preprogrammed menu of functions available to the operator via liquid crystal display 20 and pushbutton control overlay 22, and is represented schematically in FIG. 2 by mode select block 52. The measurement mode control function allows the operator to choose between a plurality of different measurement modes each characterized by a different behavior of the energizing current as a function of time. More specifically, a lookup table stored in a programmable memory 54 associated with microprocessor 46 includes digital information describing a predetermined unique current versus time relationship for each respective measurement mode, which information is used to actually generate the energizing current corresponding to a selected measurement mode. By way of example, FIG. 3 depicts a current ramp corresponding to a "standard" measurement mode, while FIG. 5 depicts a current ramp corresponding to an "alternate" measurement mode.

Figure 4:
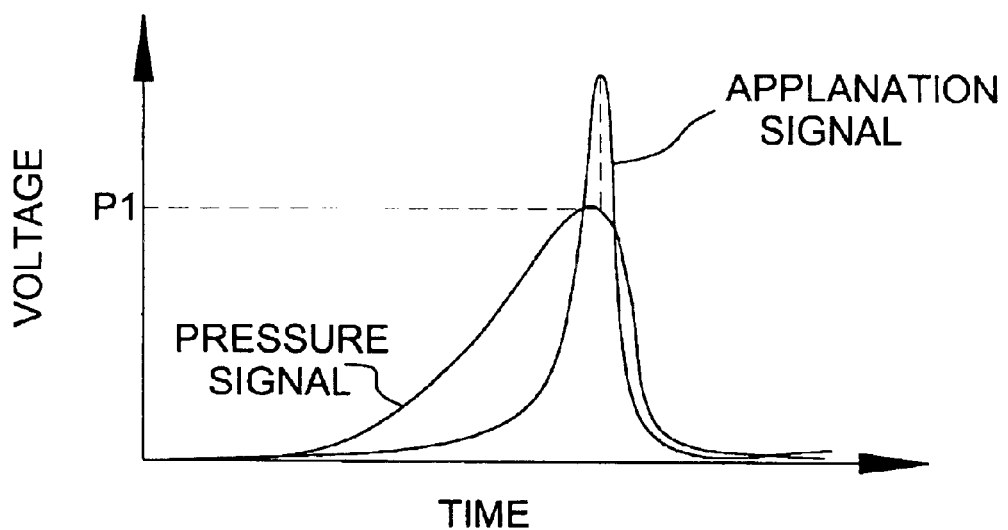
FIG. 4 is a graph of a plenum pressure signal versus time and an applanation detection signal versus time for a typical measurement stoke under the first operational mode.

The shape of the current ramp used to drive proportional solenoid 42 directly effects how the pressure within plenum chamber 38 changes as a function of time. A pressure sensor 56, for example a pressure transducer or the like, is located within plenum chamber 38 for generating a pressure signal indicative of the fluid pressure within the plenum chamber. FIG. 4 includes a plot of a pressure signal corresponding to the standard mode current ramp shown in FIG. 3. Under the standard measurement mode, measured IOP is based on correlation to the pressure within plenum chamber 38 at the moment a predetermined area of the cornea is applanated as the cornea is pushed inward from its normal convex state by the fluid pulse. In order to provide a signal indicative of the occurrence of applanation, a photosensitive detector 58 is positioned in a symmetrically oblique arrangement about test axis TA to receive corneally reflected light from emitter 60, whereby a peak signal is produced by detector 58 when the corneal surface is substantially flat for coherent reflection. Thus, the peak in the applanation signal shown in FIG. 4 represents applanation. The standard measurement mode current ramp shown in FIG. 3 increases linearly as a function of time until applanation is detected, at which time the drive current is abruptly shut off to minimize the delivery of unnecessary excess impulse energy to the eye which the patient finds uncomfortable. The ramp form shown in FIG. 3 is preferred for its simplicity and because it results in a non-linear pressure-time curve as seen in FIG. 4. As explained in commonly owned U.S. Pat. No. 6,159,148 entitled "Non-Contact Tonometer Having Non-Linear Pressure Ramp", a linearly increasing drive current produces a non-linear pressure ramp that reduces the total impulse energy delivered to the eye as compared with a constant energizing current, thereby contributing to patient comfort. Thus, in standard measurement mode, the purpose of the corresponding current ramp form is to achieve applanation while minimizing excess puff felt by the patient. Although a linearly increasing drive current is preferred for the standard mode of the present invention, other forms including a constant current may be used. IOP in the standard mode is determined according to known procedure. More specifically, the analog signal information from pressure sensor 56 and applanation detector 58 is filtered and converted to digital form for processing by microprocessor 46. The plenum pressure P1 at the time of applanation is then correlated by microprocessor 46 to an IOP value in units of mmHg (millimeters mercury) using a regression equation developed and stored in instrument memory 54 during clinical calibration relative to GAT as a reference. IOP measurement data are reported to the operator by liquid crystal display 20, and can be transmitted, preferably by wireless transmission, to a printing device and/or a remote computer.

Figure 6:
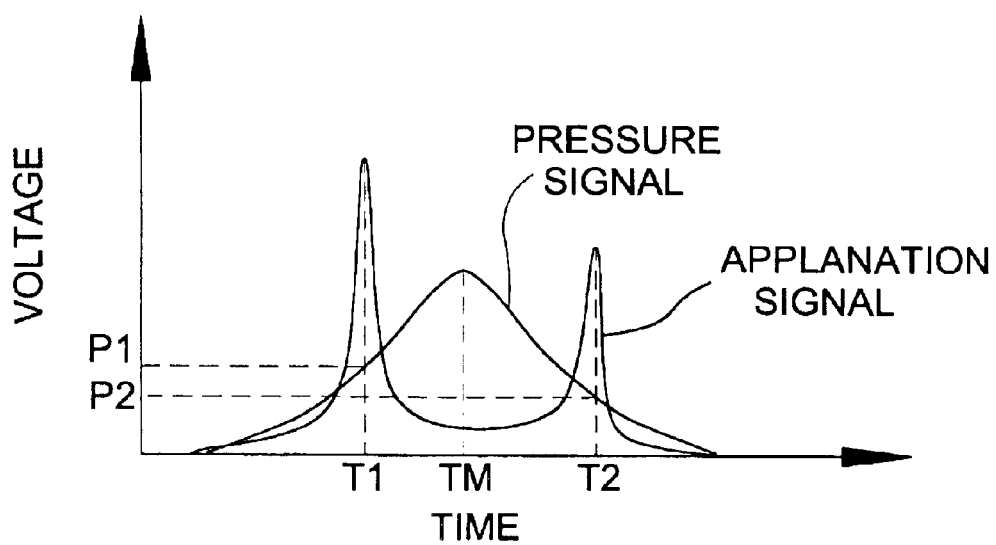
FIG. 6 is a graph of a plenum pressure signal versus time and an applanation detection signal versus time for a typical measurement stoke under the second operational mode.

In accordance with the present invention, NCT 10 is further provided with an alternate measurement mode that is primarily useful in situations where measurements taken in the standard measurement mode, and/or some other observable factor, indicate a possibility of abnormally high or low IOP, and the operator wishes to confirm whether the reading(s) obtained through the standard measurement mode are indicative of true IOP or include significant error due to corneal rigidity effects. FIG. 5 shows drive current as a function of time according to the alternate measurement mode of the preferred embodiment. As can be seen, the solenoid drive current increases linearly for a period of time longer than is necessary to achieve "inward" applanation represented by the first (left hand) peak in the applanation signal before it reverses slope and decreases at the same rate. FIG. 6 shows the resulting pressure-time curve, which is symmetrical about the instant the current reverses slope. As a result, the cornea is transfigured beyond the initial state of applanation to a state of concavity, and then returns through a second "outward" state of applanation to its original state of convexity as the plenum pressure decreases to zero. The outward applanation is represented by the second (right hand) peak in the applanation signal shown in FIG. 6.

As will be observed from FIG. 6, the time T1 of inward applanation and the time T2 of outward applanation are not equidistant from a time TM when the pressure signal reaches a maximum, and the pressure P2 associated with the outward applanation event is less than the pressure P1 associated with the first applanation event. Applicant has experimentally confirmed that this observed hysteresis pressure differential is a rate dependent effect related to the velocity of the fluid pulse, and is not dependent upon IOP. More specifically, applicant has demonstrated that as the pressure ramp is slowed down, the hysteresis decreases in a corresponding manner. Thus, the hysteresis can be thought of as a manifestation of visco-elastic losses in the dynamic system that appear when the rate of the pressure ramp is sufficiently fast and are dependent on physical properties of the cornea, as opposed to IOP.

In the preferred embodiment described herein, the hysteresis is quantified by correlating the first plenum pressure P1 to an IOP in millimeters mercury (IOP1) in the manner known and followed under the standard measurement mode, likewise correlating the second plenum pressure P2 to an IOP in millimeters mercury (IOP2), and calculating the hysteresis H by finding the difference:

$$H=IOP1-IOP2.$$

Each tonometric measurement made under the alternate measurement mode is a two-dimensional measurement, wherein the first dimension is simply an IOP value (referred to below as IOPM) based on pressure P1 associated with inward applanation, and the second dimension is hysteresis H. Thus, each alternate mode measurement is a data point comprising a first dimension datum dependent on the force necessary to applanate the cornea and a second dimension datum dependent on physical properties of the cornea itself.

As mentioned above, the alternate measurement mode is concerned with accounting for corneal rigidity effects to provide a measurement that gives the ophthalmic practitioner improved information regarding whether the patient's true IOP is abnormally high or low. The patient's measured IOP can be expressed as follows:

$$IOPM=IOPC+IOPI$$

where IOPM is measured IOP, IOPC is an equivalent IOP offset caused by corneal effects, and IOPI is the true internal ocular pressure that is of diagnostic importance. Following the observations mentioned above with regard to hysteresis H, it is assumed that IOPC is some function of hysteresis H. Thus, $$IOPC=f1\ (H)$$

By definition, $$IOPI=IOPN+EOP$$

where IOPN is a normal (average) internal pressure which is a constant approximately equal to 14.7 mmHg, and EOP is an "excess" (relative to IOPN) ocular pressure. Setting IOPN equal to a constant K1 and substituting:

$$IOPM=f1\ (H)+K1+EOP$$

By clinically measuring a statistically large population of N subjects in which EOP is approximately zero, the following relation can be written:

$$IOPM_i=f1\ (H_i)+K1;\ b=1,\ N$$

The $IOPM_i$ values can now be fitted to an r order polynomial, for example $$IOPM_i \approx \sum_{j=0,r} a_j H_i^j$$

where $a_0=k1$ and the "a" values can be determined by minimizing the least square differences—i.e., curve fitting the $IOPM_i$ versus the $H_i$ values. The quality of the assumption that the data is well fit with the r order polynomial is evaluated by calculating the traditional correlation coefficient between $IOPM_i$ and $$\sum_{j=0,r} a_j H_i^j.$$

Current data yields a correlation of about 0.9. The curve fitting is not limited to a polynomial, and other functions could be used. Even a tabular smoothed data set could be used, but the underlying physics indicate a simple relationship between second dimension data H and first dimension data IOPM.

Figure 7:
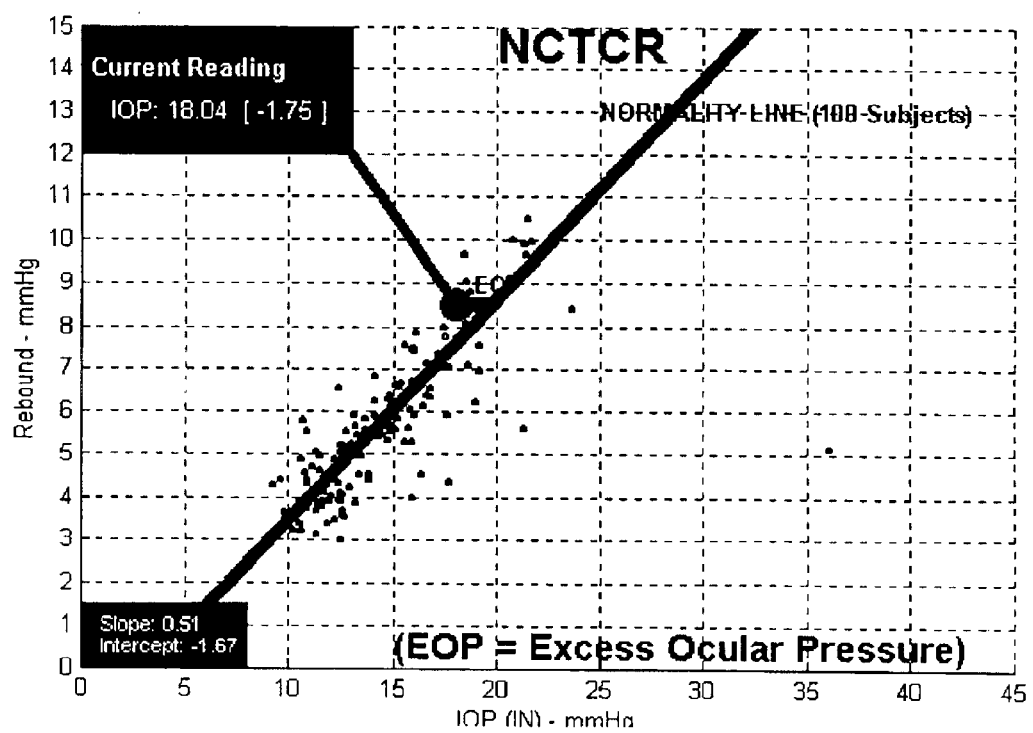
FIG. 7 is a plot showing corneal hysteresis versus measured IOP for a statistical population of eyes, a normality line fitted to the population data points, and a measurement data point taken with respect to a normal right eye of a patient to illustrate comparison of the measured data point to the normality line.
Figure 8:
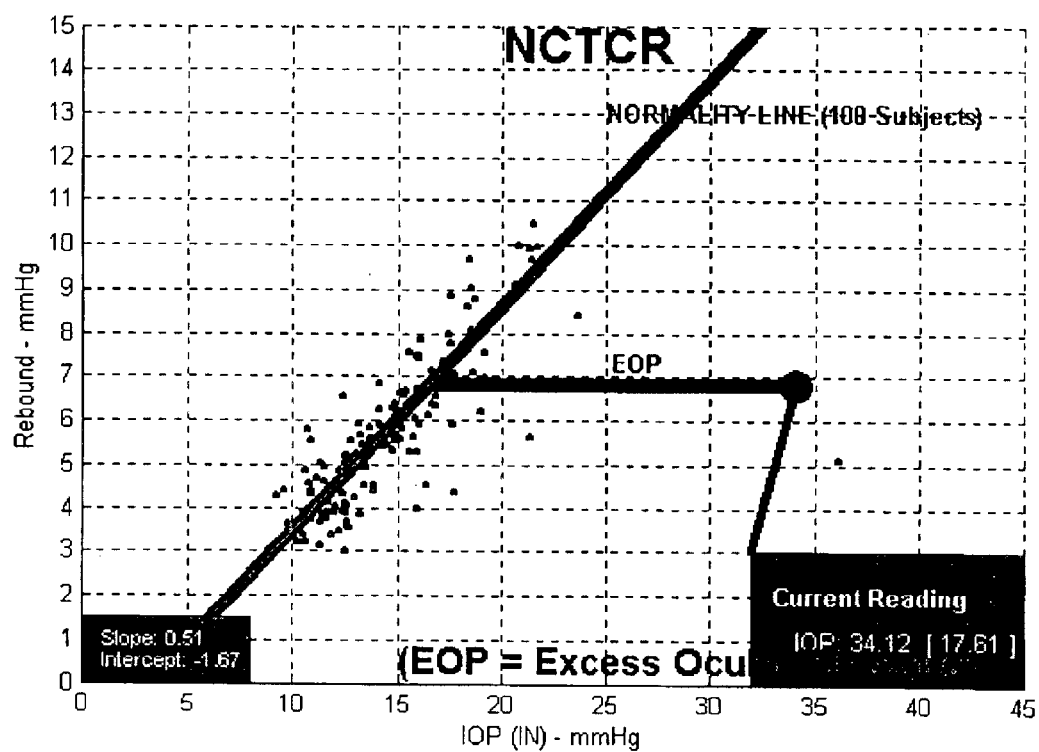
FIG. 8 is a plot similar to that of FIG. 7, however showing a measurement data point taken with respect to a left eye of the patient, wherein the left eye has an artificially elevated IOP to illustrate a high degree of difference from the normality line.

FIG. 7 is a plot of hysteresis H versus IOPM for a statistical population of one-hundred forty-six eyes measured by the same instrument. The plot shows a normality line fitted to the population data points, wherein the line has a slope of 0.51 and a y-intercept of −1.67. This functional relationship is stored in memory 60 as a part of instrument calibration. The plot also shows a two-dimensional measurement data point taken with respect to a patient's right eye wherein IOPM=18.04 mmHg, H≈8.5 mmHg, and EOP=−1.75 mmHg. The population data distribution exhibits an EOP standard deviation of 1.6 mmHg. FIG. 8 is a plot similar to that of FIG. 7 for the left eye of the same patient, however IOP has been artificially elevated by topically administered prednisolone. In FIG. 8, IOPM=34.12 mmHg, H≈6.8 mmHg, and EOP=17.61 mmHg. As can be understood from the foregoing, the alternate measurement mode enables the patient's measured IOP to be compared relative to normality as defined by a predetermined functional relationship stored in memory. The functional relationship can be a line, quadratic function, or other function fitted to the population data set. Through the use of hysteresis as a second measurement dimension, error due to corneal effects is avoided. Under prior art methodology, the patient's measured IOP would simply be compared with a population average measured IOP, with no means of ascertaining whether or to what extent a high reading is due to corneal effects rather than actual elevated IOP.

While the embodiment described above employs a set normality function derived from a clinical calibration trial, it is further possible to recalculate the normality function after each measurement or some number of measurements over the life of the instrument, whereby the normality function is updated and statistically improved as more measurements are taken.

Figure 9:
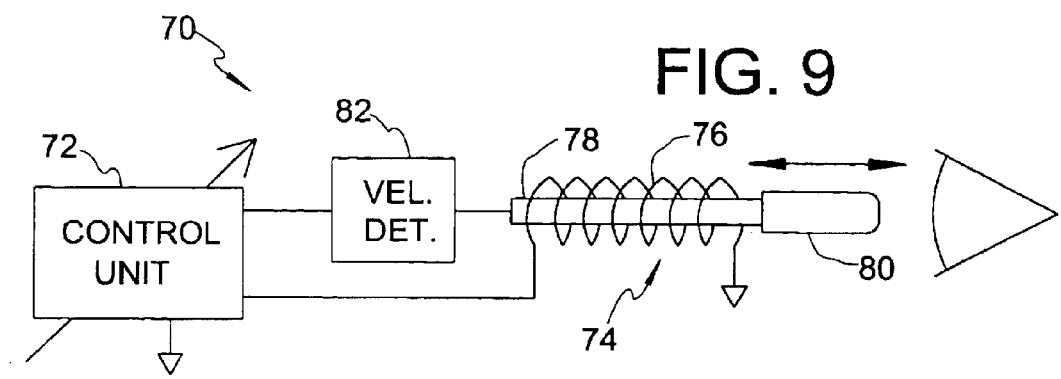
FIG. 9 is a schematic diagram of a contact type tonometer employing a method of the present invention to avoid measurement error associated with corneal rigidity.

It will be realized that the methodology used under the alternate measurement mode of non-contact tonometer 10 can also be applied by contact tonometers. For example, the pressure differential used to quantify hysteresis in the non-contact embodiment described above is analogous to a drive force differential associated with a contact tip of a contact tonometer. FIG. 9 shows a contact tonometer 70 in schematic representation as having an electronic control unit 72, a linear motor 74 having a coil 76 connected to the control unit 72 and a displaceable plunger 78, a rounded contact tip 80 fixed to a distal end of plunger 78, and a velocity detector 82 arranged to sense the velocity of plunger 78 and contact tip 80 and provide a corresponding output signal to control unit 72. Linear motor 74 is a constant force (versus position) linear proportional solenoid whose force is linearly proportional to the drive current supplied thereto, such as for example Ledex Part No. 197124-012.

Upon initiation of a signal to begin a measurement, such as by a manual trigger (not shown), the control unit 72 drives solenoid 74 "hard" until it reaches a predetermined velocity (PV). This creates a current spike at the beginning of the process before the contact tip 80 touches the eye. Upon reaching predetermined velocity PV, the solenoid current drops to zero (no force, constant velocity). At the instant contact tip 80 touches the eye, control unit 72 increases drive current, thereby increasing the force on contact tip 80, to maintain the predetermined velocity PV. The rounded shape of contact tip 80 causes the eye resistance force to increase due to the increasing area (as a function of eye depression). The visco-elastic resistance due to the corneal rigidity adds to the resistance due to IOP. The control unit detects the origin of the rising solenoid current and continues the constant velocity for a predetermined time (PT). Thus, the contact tip depresses the cornea a fixed distance (constant velocity multiplied by the predetermined time PT).

Figure 10:
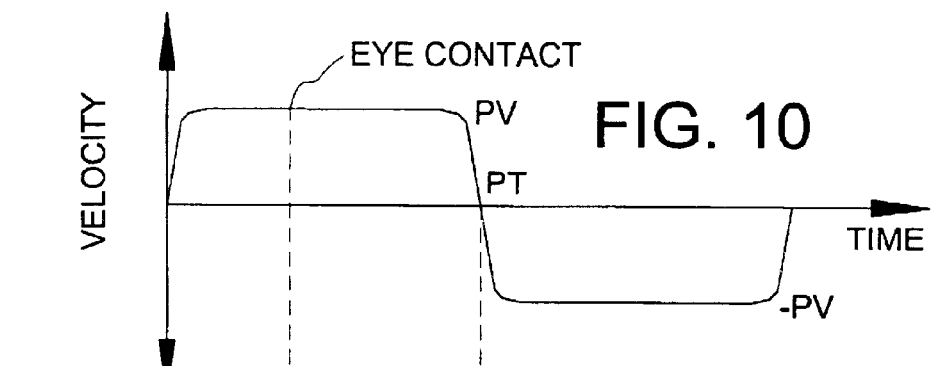
FIG. 10 is a plot of contact tip velocity versus time for a measurement stroke performed using the contact tonometer of FIG. 9.
Figure 11:
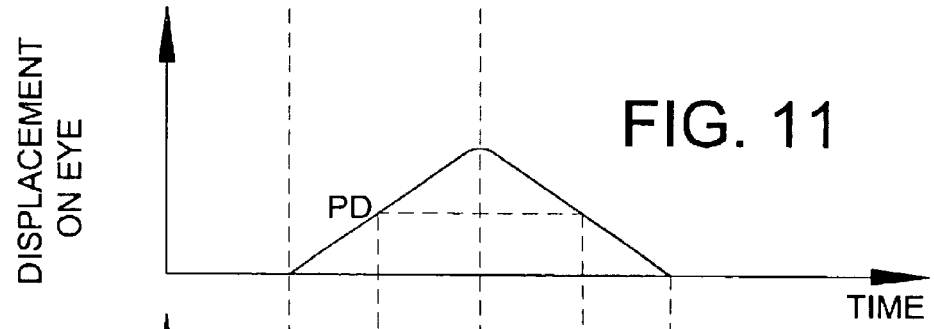
FIG. 11 is a plot of contact tip displacement on the eye versus time for the measurement stroke of FIG. 10.
Figure 12:
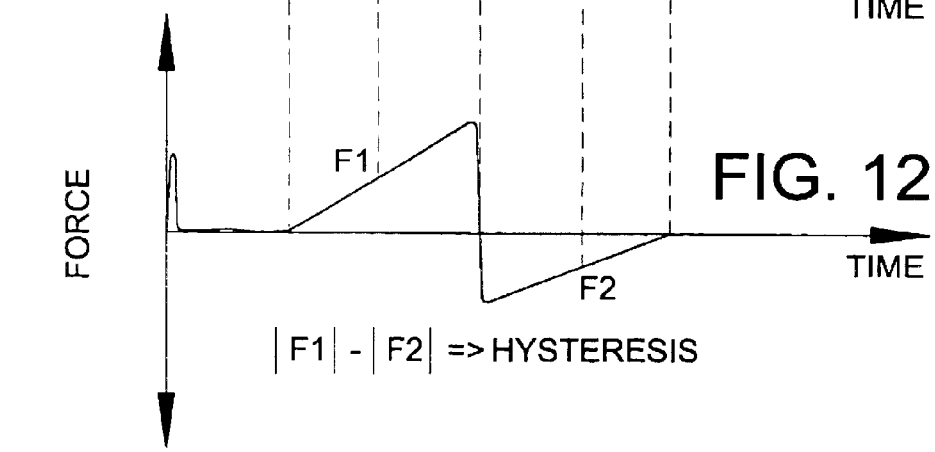
FIG. 12 is a plot of drive force on the contact tip versus time for the measurement stroke of FIG. 10.

At the end of the predetermined time PT, the control unit sets a predetermined velocity −PV equal to the negative of the first predetermined velocity PV. The linear motor 74 reverses direction and contact tip 80 withdraws from the eye. In this case, the visco-elastic forces subtract from the IOP forces. The linear motor 74 is now balancing a reduced force from the eye and therefore has a lower current. Plots of the velocity, displacement, and solenoid force are shown in FIGS. 10–12, respectively. The magnitude of the force (current to the linear motor) at the time of a predetermined displacement (PD) on the eye is determined for both the inward and outward strokes. These forces are designated F1 and F2 in FIG. 12. The difference between these two forces serves as a measure of corneal hysteresis, and the measured IOP is proportional to the average of the two forces. Consequently, contact tonometer 70 provides a two-dimensional measurement in accordance with the present invention. The entire measurement takes place in about ten milliseconds, rapid enough to produce significant visco-elastic resistance forces.

The methodology of the present invention whereby a rate dependent hysteresis effect is observed to provide a second dimension measurement datum related to corneal effects has heretofore been described in the context of a single tonometric measurement stroke. However, in a broad sense, the methodology of the present invention can be applied in the context of a pair of different measurement strokes run at different rates to allow observation of the rate dependent hysteresis effect. For example, in non-contact tonometer 10 shown in FIGS. 1 and 2, a fast measurement mode having a steep pressure ramp and a slow measurement mode having a more gradual current ramp could be used to successively measure the same eye to provide a two-dimensional data point. This approach is expressed mathematically as set forth below, wherein the following variable are defined:

$I_1$=Pressure at inward applanation (mmHg)
$I_2$=Pressure at outward applanation (mmHg)
H=Corneal hysteresis (mmHg)
R=Ramp rate ($\mu$sec/mmHg)
$I_0$=Actual internal eye pressure (mmHg)

and by definition $$H = I_1 - I_2 \tag{1}$$

$$H = \alpha R \tag{2}$$

where $\alpha$ is a constant. It is assumed that $$I_1 = I_0 + H/2$$

$$I_2 = I_0 - H/2 \tag{3}$$

Two measurements of $I_1$ are taken, designated $I_1^0$ and $I_1^1$, using two different ramp rates, R0 and R1, respectively. The two corneal hysteresis values for the two measurements are respectively designated $H^0$ and $H^1$, and $$R1 = \beta R0 \tag{4}$$

wherein $\beta$ is a scaling constant. From equation (2) by definition:

$$H^0 = \alpha R0 \tag{5}$$

$$H^1 = \alpha R1 \tag{6}$$

and from equations (3) and (4):

$$I_1^0 = I_0 + H^0/2 = I_0 + \alpha R0/2 = I_0 + \alpha R0/2 \tag{7}$$

$$I_1^1 = I_0 + H^1/2 = I_0 + \alpha R1/2 = I_0 + \alpha \beta R0/2 \tag{8}$$

Subtracting equation (6) from equation (5) and solving for hysteresis H (=$\alpha$R0) gives:

$$H^0 = \alpha R0 = 2*(I_1^0 - I_1^1)/(1-\beta) \tag{9}$$

Adding (6) and (5) yields for $I_0$:

$$I_0 = I_1^0 - [(I_1^0 - I_1^1)/(1-\beta)] \tag{10}$$

Thus, a "two shot" measurement approach using different pressure ramp rates does yield the two-dimensional data $I_1$ and H as derived previously from a single inward-outward measurement.

This approach is more time consuming and has much poorer resolution than the single measurement approach, but it is conceptually sound. One factor having a negative impact on measurement accuracy is that intraocular pressure is somewhat dependent on the point in the cardiac pulse cycle at which it is measured. A typical non-contact tonometer measurement occurs within a time frame on the order of about four to five milliseconds, whereas the normal period of a human heart pulse is on the order of about 1000 milliseconds. Therefore, in a single shot inward-outward measurement as described previously herein, there is little variation in IOP due to the status of blood flow in the eye between the inward and outward applanation events. However, in a two shot measurement scheme, the two measurements would occur at random points along the cardiac pulse cycle instead of at substantially the same point. Therefore, a two shot measurement process according to the present invention preferably includes a phase synchronization step whereby the two measurements are made at substantially the same point in the cardiac pulse cycle. For example, tonometer 10 could be equipped with a synchronizer as taught in U.S. Pat. No. 3,572,100, the disclosure of which is incorporated herein by reference.

What is claimed is:

1. A tonometry method comprising the steps of:
   providing a predetermined normal functional relationship between a first dimension and a second dimension of a two-dimensional tonometric measurement, said first dimension being dependent on a force necessary to applanate a cornea and said second dimension being dependent solely on physical properties of said cornea;
   taking said two-dimensional measurement with respect to a subject eye to obtain a first dimension datum and a second dimension datum;
   comparing said two-dimensional measurement of said subject eye with said predetermined normal functional relationship to determine a degree of difference of said measured first dimension datum from normality; and
   reporting said degree of difference.

2. The method according to claim 1, wherein said predetermined normal functional relationship is based on a set of measurement data produced by taking said two-dimensional measurement for a statistical population of eyes.

3. The method according to claim 2, wherein new measurement data are added to said set of measurement data over time and said normal functional relationship is recalculated to reflect the added new measurement data.

4. The method according to claim 2, wherein said normal functional relationship is a linear relationship fitted to said set of measurement data.

5. The method according to claim 1, wherein said two-dimensional tonometric measurement is made using a non-contact tonometer directing a fluid pulse at said cornea.

6. The method according to claim 1, wherein said two-dimensional tonometric measurement is made using a contact tonometer.

7. The method according to claim 5, wherein said first dimension datum comprises a pressure measurement datum corresponding to an inward applanation of said cornea.

8. The method according to claim 5, wherein said second dimension datum comprises a measurement datum corresponding to hysteresis associated with an inward applanation of said cornea and a subsequent outward applanation of said cornea.

9. The method according to claim 8, wherein said hysteresis measurement datum comprises a difference in pressure measurement data respectively corresponding to an inward applanation of said cornea and an outward applanation of said cornea.

10. A tonometer for measuring intraocular pressure of an eye, said tonometer comprising:
    means for applying force to a cornea of said eye to transfigure said cornea;
    means for detecting a two-dimensional data point comprising a first dimension datum at least partially dependent on a force necessary to cause said transfiguration and a second dimension datum dependent solely upon physical properties of said cornea; and
    processing means for evaluating said data point to determine a degree of difference of said measured first dimension datum from normality.

11. The tonometer according to claim 10, wherein said processing means includes memory means for storing a predetermined normal functional relationship between said first dimension datum and said second dimension datum for a statistical population of eyes, and wherein said processing means evaluates said data point relative to said predetermined normal functional relationship.

12. The tonometer according to claim 10, wherein said second dimension datum is related to hysteresis between a first transfigured state of said cornea occurring as said cornea is pushed inward from its original convex shape and a subsequent second transfigured state of said cornea as said cornea returns to its original convex state.

13. The tonometer according to claim 12, wherein said tonometer is a non-contact tonometer, and said first and second transfigured states are states of corneal applanation.

14. The tonometer according to claim 12, wherein said tonometer is a contact tonometer, and said first and second transfigured states are defined by a predetermined displacement of a contact tip of said contact tonometer.

15. A method of detecting corneal hysteresis comprising the steps of:
    (A) exerting pressure on a cornea to deform said cornea from a natural state of convexity through a first state of applanation to a state of concavity;
    (B) decreasing said exerted pressure to allow said cornea to return from said state of concavity through a second state of applanation to said natural state of convexity;
    (C) observing a first pressure associated with said first state of applanation and a second pressure associated with said second state of applanation; and
    (D) calculating a pressure differential between said first and second pressures, said pressure differential being indicative of said corneal hysteresis.

16. A tonometry method comprising the steps of:
    (A) transfiguring a cornea of a subject eye by increasing force on said cornea at a first rate, and detecting a first value corresponding to a first force at which a predetermined state of corneal transfiguration occurs;
    (B) again transfiguring said cornea by increasing force on said cornea at a second rate differing from said first rate, and detecting a second value corresponding to a second force at which said predetermined state of corneal transfiguration occurs;
    (C) deriving a two-dimensional measurement data point from said first value and said second value, said two-dimensional measurement data point comprising a first dimension datum corresponding to either said first value or said second value and a second dimension datum corresponding to a difference between said first value and said second value;
    (D) providing a predetermined normal functional relationship between said first dimension datum and said second dimension datum;
    (E) comparing said two-dimensional measurement data point for said subject eye with said predetermined normal functional relationship to determine a degree of difference of said first dimension datum from normality; and
    (F) reporting said degree of difference.

17. The method according to claim 16, wherein said step (A) is performed using a non-contact tonometer to direct an air pulse at said cornea, and said step (B) is performed using said non-contact tonometer to direct another air pulse at said cornea.

18. The method according to claim 17, wherein said air pulse and said another air pulse are synchronized with respect to a cardiac pulse cycle of said patient.

* * * * *